United States Patent [19]
Takai et al.

[11] Patent Number: 5,656,232
[45] Date of Patent: Aug. 12, 1997

[54] TOPSHEET OF BODY FLUID ABSORPTIVE ARTICLES AND METHOD FOR MAKING SAME

[75] Inventors: Hisashi Takai; Tsutomu Kido, both of Kawanoe, Japan

[73] Assignee: Uni-Charm Corporation, Ehime-ken, Japan

[21] Appl. No.: 492,345

[22] Filed: Jun. 19, 1995

Related U.S. Application Data

[62] Division of Ser. No. 230,517, Apr. 20, 1994, abandoned.

[30] Foreign Application Priority Data

Apr. 27, 1993 [JP] Japan ................................. 5-101190

[51] Int. Cl.⁶ ............................................ B32B 3/10
[52] U.S. Cl. ........................... 264/518; 264/112; 264/115; 156/62.2; 156/167
[58] Field of Search ................................. 264/112, 115, 264/518; 156/62.2, 167

[56] References Cited

U.S. PATENT DOCUMENTS 3,542,028  11/1970  Beebe et al. .

5,242,632  9/1993  Mende ............................................ 264/6

FOREIGN PATENT DOCUMENTS

| 0040447 | 11/1981 | European Pat. Off. . |
|---|---|---|
| 0235309 | 9/1987 | European Pat. Off. . |
| 0304617 | 3/1989 | European Pat. Off. . |
| 2270874 | 3/1994 | United Kingdom . |
| 2272917 | 6/1994 | United Kingdom . |

*Primary Examiner*—Mary Lynn Theisen
*Attorney, Agent, or Firm*—Lowe, Price, LeBlanc & Becker

[57] ABSTRACT

A topsheet of body fluid absorptive articles comprising a first sheet made of thermoplastic synthetic resin sheet and having liquid passages each downwardly extending therethrough and a second sheet containing 70 to 100% by weight of cellulose fibres bonded to said first sheet around lower openings of the respective liquid passages and comprises mechanically intertwined fibres only. The second sheet has a density higher than a density of fibres contained in the liquid-absorbent core.

4 Claims, 2 Drawing Sheets

TOPSHEET OF BODY FLUID ABSORPTIVE ARTICLES AND METHOD FOR MAKING SAME

This application is a division of application Ser. No. 08/230,517 filed Apr. 20, 1994, now abandoned.

BACKGROUND OF THE INVENTION

The present invention relates to a topsheet used for body fluid absorptive articles such as sanitary napkins and disposable diapers and also to a method for making the topsheet.

It is well known to form a topsheet used for body fluid absoptive articles, to provide this sheet with a plurality of liquid passages each extending through the sheet from an upper opening to a lower opening so that the upper surface comes in contact with a wearer's skin, and the lower openings of the liquid passages are in contact with a liquid-absorbent core, and thus body fluids are introduced into the liquid-absorbent core under a capillary action occurring within the respective liquid passages.

For example, Japanese Patent Publication No. 1982-17081 discloses a technique such that a topsheet made of polyethylene sheet is provided with liquid passages each in the form of truncated cone-shaped capillary tube and a lower end of each liquid passage is arranged in close contact with a liquid-absorbent core.

Japanese patent application Disclosure No. 1995-58950 discloses a technique Such that thermoplastic synthetic fibres are melt-blown to form nonwoven fabric which is then formed with liquid passages and fibrous fluff is formed around lower openings of the liquid passages to obtain a topsheet.

In both of the above-mentioned prior techniques, the lower end of each liquid passage should be always in close contact with the liquid-absorbent core. However, the topsheet which is thin and less rigid is readily wrinkled during the practical use of the body fluid absorptive articles and, in consequence, the lower end of each liquid passage is separated from the liquid-absorbent core, preventing the body fluids from being smoothly transferred into the liquid-absorbent core.

Generally, the soft touch is indispensable to the body fluid absorptive articles. For example, in the case of the liquid-absorbent core formed of fluff pulp, a density thereof is limited, since an excessively high density of the fluff pulp would give a wearer the unpleasant stiff touch. However, an excessively low density of the fluff pulp would reduce the diffusibility of the body fluids. As a result, the body fluids transferring from the liquid passages to the liquid-absorbent core can not rapidly diffuse laterally from the lower openings and the body fluids stay on the topsheet for a correspondingly longer time, giving a wearer the discomfortable feel of wetness.

Accordingly, it is a principal object of the invention to solve the problem encountered by the previously mentioned prior techniques by composing a topsheet from a first sheet and a second sheet, bonding the second sheet to the first sheet around lower openings of respective liquid passages formed through the first sheet and adjusting a density of the second sheet at a level of a density of a liquid-absorbent core.

SUMMARY OF THE INVENTION

The object set forth above is achieved, according to an aspect of the invention, by a topsheet for body fluid absorptive articles comprising this liquid-permeable topsheet including a plurality of liquid passages each extending therethrough from an upper opening to a lower opening and a skin-contacting area extending continuously around the upper openings of said liquid passages, a liquid-impermeable backsheet and a liquid-absorbent core sandwiched between these sheets, said topsheet comprising: a first sheet made of thermoplasitc synthetic resin sheet and provided with said liquid passages and said skin-contacting area; and a second sheet underlying said first sheet and bonded thereto around the lower openings of the respective liquid passages; wherein said second sheet is made of mechanically intertwined fibres only and has a density higher than a density of fibres contained in said liquid-absorbent core.

Preferably, the second sheet of said topsheet is fibre-oriented in the longitudinal direction of said topsheet and the second sheet is composed of a mixture of 70 to 100% by weight of cellulose fibres and 30 to 0% by weight of thermoplastic synthetic fibres.

The object set forth above is achieved, according to another aspect of the invention, by a method for making a topsheet used in body fluid absorptive articles comprising this liquid-permeable topsheet including a plurality of liquid passages each extending therethrough from an upper opening to a lower opening and a skin-contacting area extending continuously around the upper openings of said liquid passages, a liquid-impermeable backsheet and a liquid-absorbent core sandwiched between these sheets, said method comprising steps of: blowing molten fibres from a melt-blow extruder against a forming die having a plurality of protrusions dimensioned substantially in a uniform height, said protrusions having flat tops, to form melt-blown nonwoven fabric following the configuration of said forming die; bringing a heating element in contact with said melt-blown nonwoven fabric at said tops to form openings each defined by an indented periphery; and feeding fibrous web comprising mechanically intertwined fibres only and having a density higher than a density of fibres contained in said liquid-absorbent core onto said melt-blown nonwoven fabric and thereby mechanically entwining said fibrous web around said indented peripheries to obtain said topsheet.

Preferably, the fibrous web is fibre-oriented in the longitudinal direction of said topsheet. The fibrous web is preferably composed of a mixture of 70 to 100% by weight of cellulose fibres and 30 to 0% by weight of thermoplastic synthetic fibres.

In the topsheet constructed in the above-mentioned manner according to the invention, the second sheet is bonded to the first sheet around the lower openings of the respective liquid passages and thereby integrated with the first sheet. Thus, the topsheet has its rigidity improved sufficiently to prevent the topsheet from being wrinkled and to restrict the deformation of the lower openings. Consequently, the liquid passages are not readily clogged. The periphery of each lower opening is bonded to the second sheet having a density higher than a density of the fibres contained by the liquid-absorbent core, on one hand, and the second sheet is in contact with the liquid-absorbent core, on the other hand, so the body fluids having reached the lower openings of the respective liquid passages not only can be smoothly transferred immediately downward through the second sheet into the liquid-absorbent core but also can be rapidly diffused through the second sheet in the surface-direction and then transferred into the liquid-absorbent core.

The second sheet is fibre-oriented in a desired direction and the body fluids can be easily diffused particularly in the direction corresponding to said fibre-orientation. For example, said fibre-orientation may be selected so as to coincide with the longitudinal direction of the body fluid absorptive goods to assure that the body fluids be rapidly diffused longitudinally of the liquid-absorbent core and the entire liquid-absorbent core be efficiently used.

According to the method of the invention for making the topsheet, the openings respectively defined by the indented peripheries can be formed by melting the protrusions formed on the melt-blown nonwoven fabric and the fibrous web is formed by mechanically intertwined fibres so that the fibres of this web may be easily disentangled and reliably entangled around said peripheries. With a consequence, the melt-blown nowoven fabric can be easily integrated with the fibrous web.

BRIEF DESCRIPTION OF THE DRAWINGS

A topsheet according to the invention and a method for making it will be described more in detail with reference to the accompanying drawing, in which.

PREFERRED EMBODIMENTS OF THE INVENTION

Figure 1:
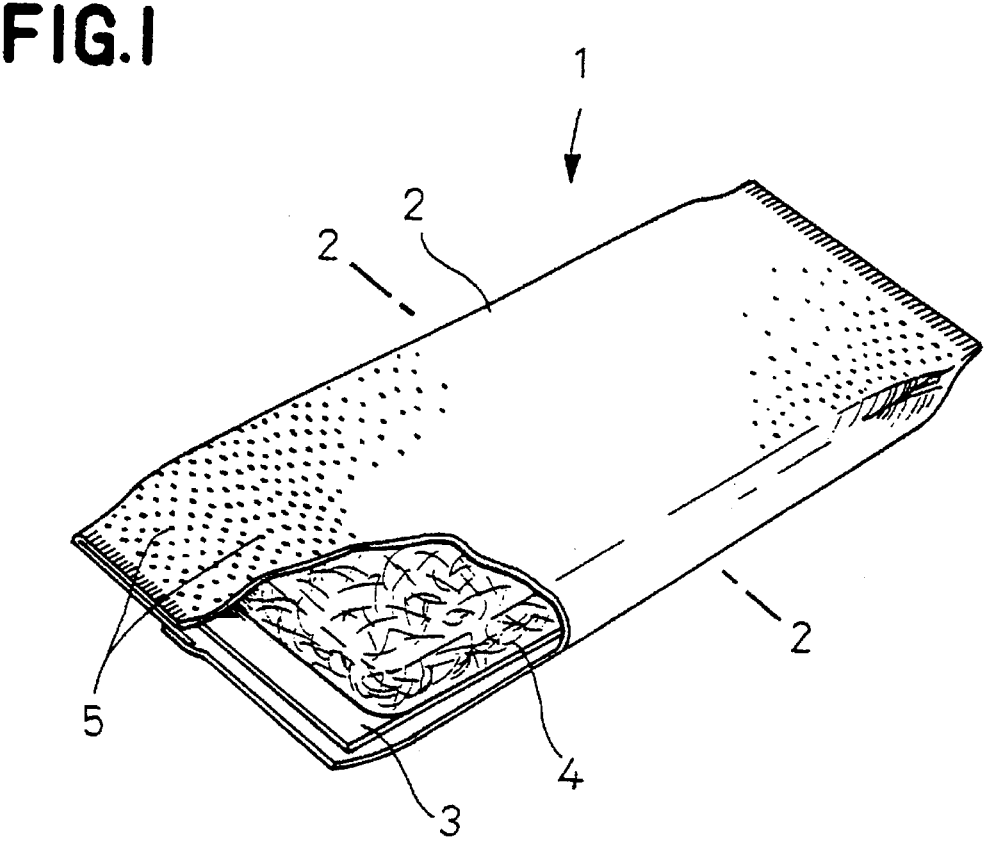
FIG. 1 is a perspective view of a sanitary napkin.

Referring to FIG. 1 a sanitary napkin 1 utilizing a topsheet 2 of the invention is shown as partially broken away. The napkin 1 comprises the liquid-permeable topsheet 2, a liquid-impermeable backsheet 3 and a liquid-absorbent core 4 sandwiched between these sheets 2, 3. The topsheet 2 entirely wraps the liquid-absorbent core 4 with overlapped opposite side edges thereof bonded to each other on a rear side of the napkin 1 and with upper and lower layers of longitudinally opposite ends thereof bonded to each other along longitudinally opposite ends of the napkin 1, respectively. The backsheet 3 is interposed between the topsheet 2 and the liquid-absorbent core 4 on the rear side of the napkin 1.

Figure 2:
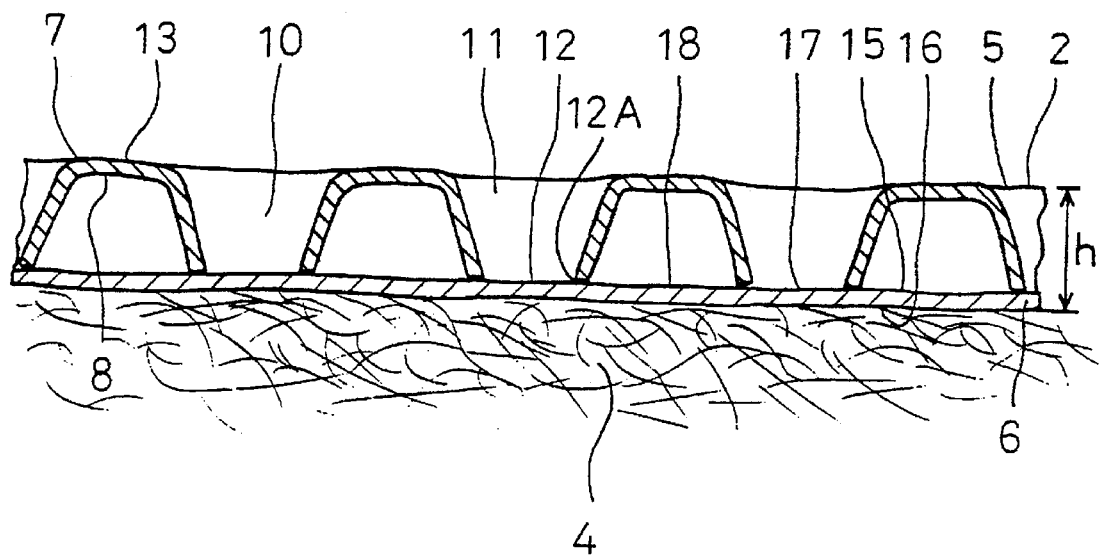
FIG. 2 is a fragmentary sectional view taken along a line 2—2 in FIG. 1.

FIG. 2 is a fragmentary sectional view taken along a line 2—2 in FIG. 1, schematically showing a state in which the topsheet 2 is in contact with the liquid-absorbent core 4. The topsheet 2 comprises an upper sheet 5 lying on the side of a wearer's skin and a lower sheet 6 lying on the side of the liquid-absorbent core 4, the upper sheet 5 has an upper surface 7, a lower surface 8, liquid passages 10 each extending from the upper surface 7 to the lower surface 8 over a height of h, and a skin-contacting area 13 continuously extending around upper openings 11 of the respective liquid-passages 10. The lower sheet 6 has an upper surface 15, a lower surface 16, and an exposed area 17 within the respective liquid passages 10, and a non-exposed area 18 opposed to the skin-contacting area 13. The lower surface 16 is planar at least over the exposed area 17 or rounds out toward the liquid-absorbent core 4, i.e., does not rise into the respective liquid passages 10, so the lower surface 16 is easily brought into close contact with the liquid-absorbent core 4. Over the non-contacting area 18, the lower surface 16 is preferably similar to the exposed area 17.

In the upper sheet 5, lower openings 12 of the liquid passage 10 has its periphery 12A indented by plurality of irregularities and fluffs. On the other hand, the lower sheet 6 comprises a web formed by fibres mechanically inter- twined together and entwined also with the periphery so as to be integrated with the upper sheet 5 and thereby to form the topsheet 2.

The upper sheet 5 is formed by film of thermoplastic synthetic resin or nonwoven fabric sheet of thermoplastic synthetic fibres and hydrophobic. The synthetic resin film may be, for example, polyethylene film having a thickness of 0.01 to 0.10 mm and the nowoven fabric sheet may be, for example, melt blown nonwoven fabric having a weight per unit area of 5 to 100 g/m$^2$.

The lower sheet 6 is formed by fibrous web comprising 70 to 100% by weight of cellulose fibres such as pulp or rayon mixed with 30 to 0% by weight of thermoplastic synthetic fibres. The lower sheet 6 is more hydrophilic than the upper sheet 5 and has a density higher than a density of the fibres forming the liquid-absorbent core 4. When the liquid-absorbent core 4 is formed, for example, by a mixture of fluff pulp and high absorption polymer powders, it is preferred to adjust the density of the lower sheet 6 at a level higher than a density of said fluff pulp. Usually, the density of such fluff pulp is selected in a range from 0.02 to 0.1 g/cm$^3$. Many of the fibres forming the lower sheet 6 have an orientation longitudinal of the napkin 1 and body fluids easily diffuse particularly in the direction corresponding to said orientation under capillary action. If it is desired, the lower sheet 6 primarily composed of cellulose fibres may be added and mixed with 30% by weight or fewer of thermoplastic synthetic fibres to achieve the diffusibility of body fluids higher than such diffusibility achieved by the lower sheet formed by 100% by weight of cellulose fibres.

Each liquid passage 10 of the upper sheet 5 may be a capillary tube tapered toward to the liquid-absorbent core 4, a capillary tube tapered in the reverse direction, or a cylindrical capillary tube of a uniform diameter. The liquid passage 10 preferably has a length of 0.1 to 7 mm. The upper and lower openings 11, 12 may be circular, polygonal or of any other appropriate shape and its diameter is preferably 0.3 to 7 mm.

Figure 3:
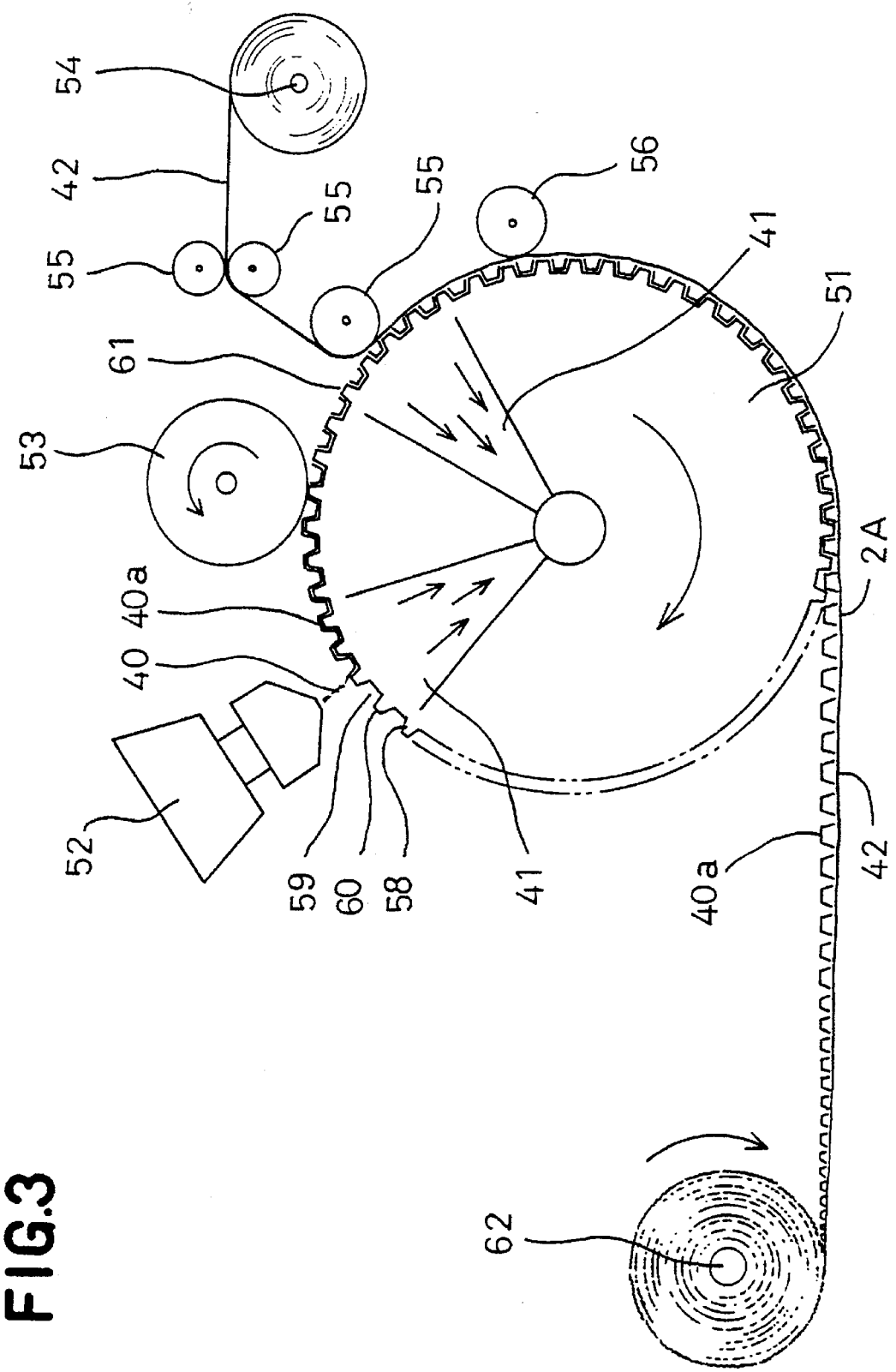
FIG. 3 is a diagram schematically illustrating a production line for forming the topsheet.

Referring to FIG. 3, a production line for forming the topsheet 2 is schematically illustrated. This production line comprises a clockwise rotatabel roll 51 serving as a forming die, a melt-blow extruder 52 opposed to the roll 51, a heating roll 53 adapted to be adjusted at a desired temperature, a fibrous web feeder 54 and a take-up means 62.

The roll 51 is provided around its outer peripheral surface with a plurality of protrusions 58 having a substantially uniform height and each having a flat top and indents 59 around the respective protrusions 58. The entire periphery of the roll 51 is provided with a plurality of fine through-holes (not shown) communicating with suction means 41 provided within the roll 51.

Molten fibres 40 are blown from the melt-blow extruder 52 against the outer peripheral surface of the roll 51 under the action of the suction means 41 to form a melt-blown nonwoven fabric 40a following the protrusions 58 and the indents 59.

The heating roll 53 is arranged to come in contact with flat tops 60 of the respective protrusions 58 and melts the nonwoven fabric 40a interposed between the heating roll 53 and the flat tops 60 on the respective flat tops 60 so as to form openings 61.

The fibrous web feeder 54 feeds a web 42 through a pair of guide rolls 55 onto the nonwoven fabric 40a which has been formed with the openings 61 under the action of the suction means 41 and simultaneously the web 42 is entwined with the melt-blown nonwoven fabric around the respective openings 61 under the action of a pressure roll 56. The melt-blown nonwoven fabric 40a and the web 42 integrated in this manner are taken up by the take-up means 62 to obtain an uncut roll 2A for the topsheet 2. This uncut roll 2A will be cut into individual sheets dimentioned appropriatedly to be used for individual napkins 1.

The construction of the uncut roll 2A made by the abovementioned method is related with the construction of the individual topsheet 2 which is cut from the uncut roll 2A so that the melt-blown nonwoven fabric 40a and the web 42 form the upper and lower sheets 5, 6, respectively; the portions deformed by the protrusions and the indents form the liquid passages 10 and the skin-contacting area 13, respectively; and the portions of the web overlying the respective tops 60 of the protrusions form the exposed area 17. The exposed area 17 does not rise toward the upper openings 11 in the topsheet 1 and is reliably brought in contact with the liquid-absorbent core 4 when used in the napkin 1, since the tops 60 are flat.

The fibrous web 42 is formed by web comprising mechanically intertwined fibres only such as random web, card web, air-laid web or nonwoven fabric obtained by subjecting any of these webs to entwinement under a high pressure of water jet and adjusted to have a density higher than a density of the fibers contained in the liquid-absorbent core 4 to be actually employed. The fibrous web 42 contains hydrophilic cellulose fibres such as pulp or rayon occupying 70 to 100% by weight with respect to a total amount of used fibres and, if desired, such hydrophilic fibres may be mixed with hydrophobic thermoplastic synthetic fibres of 30 to 0% by weight. Such web or nonwoven fabric is usually fibre-oriented in the machine direction during its making process and therefore the web 42 is fed and/or cut so that the fibre-orientation may coincide with the longitudinal direction of the napkin 1 to be manufactured.

The topsheet of the invention allows the deformation of the liquid passages to be effectively restricted by bonding the lower sheet to the upper sheet.

The lower sheet is adjusted to have a density higher than a density of the liquid-absorbent core and consequently the body fluids, after they have reached the lower end of each liquid passage, not only immediately penetrate through the lower sheet into the liquid-absorbent core but also rapidly diffuse through the lower sheet in the surface-direction and then penetrate therethrough downward into the liquid-absorbent core. In this manner, with the body fluid absorptive articles adopting the topsheet of the invention, the body fluids are absorbed into the liquid-absorbent core over a ralatively large area and a time for which the body fluids stay on the topsheet is correspondingly shortened. With a consequence, the unpleasant feel of wetness is alleviated.

The lower sheet may be fibre-oriented in the desired direction to accelerate diffusion of the body fluids in this direction and such diffusion may be further promoted by mixing the thermoplastic synthetic fibres into the lower sheet.

The web comprising mechanically intertwined fibres only is used as the lower sheet, so the fibres easily become disentangled and readily entwine around the indented periphery of each liquid passage's lower opening. Such feature facilitates the integration of the upper and lower sheets into the topsheet.

What is claimed is:

1. A method for making a liquid-permeable topsheet used in a body fluid absorptive article, said article including said liquid-permeable topsheet having a plurality of liquid passages each extending therethrough from an upper opening to a lower opening and a skin-contacting area extending continuously around the upper openings of said liquid passages, a liquid-impermeable backsheet and a liquid-absorbent core sandwiched between these sheets, said method comprising steps of:

blowing molten fibers from a melt-blow extruder against a forming die having a plurality of protrusions dimensioned substantially in a uniform height, said protrusions having flat tops, to form melt-down nonwoven fabric following the configuration of said forming die;

bringing a heating element in contact with said melt-blown nonwoven fabric at said tops to form openings each defined by an indented periphery; and feeding fibrous web comprising mechanically intertwined fibers only and having a density higher than a density of fibers contained in said liquid-absorbent core onto said melt-blown nonwoven fabric and thereby mechanically entwining said fibrous web around said indented peripheries to obtain said topsheet.

2. A method according to claim 1, wherein said fibrous web is fibre-oriented in the longitudinal direction.

3. A method according to claim 1, wherein said fibrous web comprises a mixture of 70 to 100% by weight of cellulose fibres and 30 to 0% by weight of thermoplastic synthetic fibres.

4. A method for making a topsheet used in a body fluid absorptive article, comprising the steps of melt-blowing molten fibers against a forming die having protrusions of substantially uniform height with substantially flat tops, to form melt-blown nonwoven fabric following the configuration of said forming die;

contacting the melt-blown nonwoven fabric with a heating element at said substantially flat tops to form openings therein; and mechanically entwining said fabric with a fibrous web at said openings.

* * * * *